United States Patent [19]
Cook et al.

[11] 4,011,215
[45] * Mar. 8, 1977

[54] 3-CHLOROALKYLCARBAMOYLOX-
YMETHYL-7-[2-(FUR-2-YL)-2-METHOX-
YIMINOACETAMIDO]CEPH-3-EM-4-CAR-
BOXYLIC ACIDS AND PHYSIOLOGICALLY
ACCEPTABLE SALTS OR OXIDES
THEREOF

[75] Inventors: Martin C. Cook, Liverpool; Gordon I. Gregory, Chalfont St. Peter; Janice Bradshaw, Harrow, all of England

[73] Assignee: Glaxo Laboratories Limited, Greenford, England

[ * ] Notice: The portion of the term of this patent subsequent to Aug. 10, 1993, has been disclaimed.

[22] Filed: Aug. 1, 1975

[21] Appl. No.: 601,397

[30] Foreign Application Priority Data

Aug. 15, 1974 United Kingdom ............. 36012/74

[52] U.S. Cl. .......................... 260/243 C; 424/246
[51] Int. Cl.$^2$ ....................... C07D 501/20
[58] Field of Search ............................ 260/243 C

[56] References Cited

UNITED STATES PATENTS 3,573,294  3/1971  Long et al. .............. 260/243 C
3,946,219  12/1970  Long et al. .............. 260/243 C Primary Examiner—Nicholas S. Rizzo
Attorney, Agent, or Firm—Bacon & Thomas

[57] ABSTRACT

Cephalosporin antibiotics in which the 7β-acylamido group is syn 2-furyl-2-methoxyiminoacetamido and in which the 3-position substituent is a chloroalkylcarbamoyloxymethyl group exhibit high antibacterial activity against a broad range of gram positive and gram negative organisms, particularly high stability to β-lactamases produced by various organisms, and stability in vivo. The compounds are syn isomers or exist as mixtures of syn and anti isomers containing at least 90% of the syn isomer.

6 Claims, No Drawings

3-CHLOROALKYLCARBAMOYLOXYMETHYL-7-[2-(FUR-2-YL)-2-METHOXYIMINOACETAMIDO]-CEPH-3-EM-4-CARBOXYLIC ACIDS AND PHYSIOLOGICALLY ACCEPTABLE SALTS OR OXIDES THEREOF

This invention is concerned with improvements in or relating to antibiotics of the cephalosporin series.

The cephalosporin compounds in this specification are named with reference to "cepham" after *J. Amer. Chem. Soc.*, 1962, 84, 3400, the term cephem referring to the basic cepham structure with one double bond.

Many cephalosporin compounds possessing a degree of antibacterial activity are known in the art, these compounds possessing $\Delta^3$ unsaturation and ordinarily being substituted at the 3-position by a methyl or substituted methyl group and at the 7$\beta$-position by an acylamido group. It is now well recognised that the antibiotic properties of a particular ceph-3-em-4-carboxylic acid are predominantly controlled by the nature of both the 7$\beta$-acylamido group thereof and the 3-position substituent which the compound carries; considerable research has been undertaken to find combinations of such groups which will yield antibiotics with particular properties.

Cephalosporin antibiotics are widely used in the treatment of diseases caused by pathogenic bacteria in human beings and animals, for example in the treatment of diseases caused by bacteria which are resistant to other antibiotics such as penicillin compounds and in the treatment of penicillin-sensitive patients. In many applications it is desirable to employ a cephalosporin antibiotic which exhibits activity against both gram positive and gram negative microorganisms, and a significant amount of reasearch has been directed to the development of improved broad spectrum cephalosporin antibiotics.

The practical utility of a significant number of known commercial and experimental cephalosporin antibiotics is limited by their relatively high susceptibility to the $\beta$-lactamases which are produced by many bacteria. A desirable property of a broad spectrum cephalosporin antibiotic is therefore that it should exhibit substantial resistance to $\beta$-lactamases, including those produced by gram negative microorganisms.

A further difficulty with many cephalosporin antibiotics intended for therapeutic applications is that they are subject to degradation in vivo. Thus a significant number of known cephalosporin antibiotics have been found to suffer the disadvantage that following administration they are deactivated, often rapidly, by enzymes (e.g. esterases) present in the body.

As a result of prolonged studies of numerous cephalosporin compounds we have now found a class of cephalosporin antibiotics having a particular combination of 7$\beta$-acylamido group and 3-position substituent which endows the compounds with good broad spectrum activity coupled with the above-described desiderata of high $\beta$-lactamase stability and good stability in vivo. These compounds are characterised in that the 7$\beta$-acylamido group is a 2-furyl-2-methoxyiminoacetamido group which is substantially in the syn configuration (as hereinafter defined) and that the 3-substituent is a chloroalkylcarbamoyloxymethyl group.

The present invention, therefore, provides antibiotic compounds of the general formula

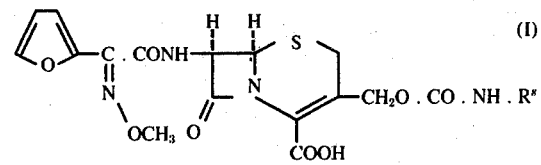

(where $R^s$ represents a $C_1$–$C_4$ alkyl group substituted by chlorine) and non-toxic derivatives of these acids, the compounds being syn isomers or existing as mixtures of syn and anti isomers containing at least 90% of the syn isomer. Most preferably the compounds are the syn isomers essentially free from the corresponding anti isomers.

The compounds of the invention are defined as having the syn (cis) isomeric form as regards the configuration of the methoxy ($OCH_3$) group with respect to the carboxamido group. In this specification the syn configuration is structurally denoted thus:

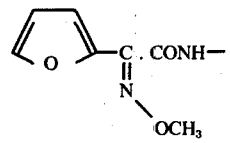

The syn configuration is assigned on the basis of the work of Ahmad and Spenser as reported in *Can. J. Chem.* 1961, 39, 1340.

The term "non-toxic" as applied to derivatives of the compounds of the invention means those derivatives which are physiologically acceptable in the dosage at which they are administered. Such derivatives may include, for example, salts, biologically acceptable esters, 1-oxides and solvates (especially hydrates) of the compound.

Salts which may be formed, where applicable, from the compounds according to the invention include inorganic base salts such as alkali metal (e.g. sodium and potassium), alkaline earth metal (e.g. calcium) and organic base (e.g. procaine, phenylethylbenzylamine, dibenzylethylenediamine, ethanolamine, diethanolamine, triethanolamine and N-methylglucosamine) salts. The salts may also be in the form of resinates, formed e.g. with a polystyrene resin or cross linked polystyrenedivinylbenzene copolymer resin containing amino or quaternary amino groups.

The group $R^s$ in formula I may be, for example, chloromethyl, chloroethyl etc., but is advantageously 2-chloroethyl.

The antibiotic compounds of the invention are characterized by their antibacterial activity against a range of gram-positive and gram-negative organisms, which may render them useful in the treatment of a variety of diseases caused by pathogenic bacteria in human beings and animals.

An important compound falling within general formula I by virtue of its broad spectrum antibiotic properties, stability in the presence of human serum and high stability to $\beta$-lactamases produced by a variety of organisms is (6R,7R)-3-(N-2-chloroethylcarbamoyloxymethyl)-7-[2-(fur-2-yl)-2-methoxyiminoacetamido]-ceph-3-em-4-carboxylic acid (syn isomer), having the formula

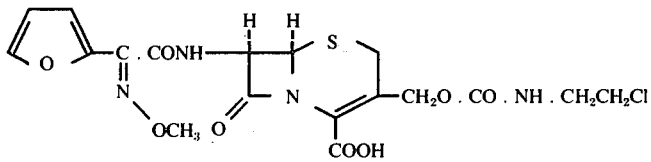

for example as its sodium or potassium salt.

The compounds according to the invention may be prepared by any convenient method.

According to one embodiment of the invention we provide a process for the preparation of a compound of general formula I (as hereinbefore defined) and non-toxic derivatives thereof which comprises either (A) condensing a compound of the formula

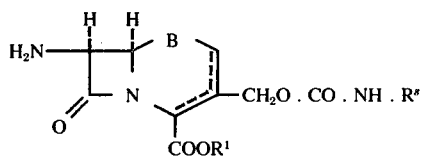

(wherein B is >S or >S→O, $R^1$ is hydrogen or a carboxyl blocking group, $R^s$ has the above-defined meaning, and the dotted line bridging the 2-, 3- and 4-positions of formula (II) indicates that the compound may be a ceph-2-em or a ceph-3-em compound) with an acylating agent corresponding to the acid:

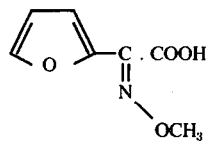

or with an acylating agent corresponding to an acid which is a precursor for the acid (III); or (B) reacting a compound of the formula

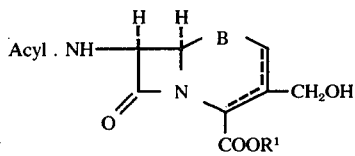

(wherein Acyl is the group syn-2-(fur-2-yl)-2-methoxyiminoacetyl or a precursor therefor;

B, $R^1$ and the dotted line have the above meanings) with an isocyanate of formula $R^s$.NCO (wherein $R^s$ has the above defined meaning) whereafter, if necessary and desired in each instance, any of the following reactions (C), in any desired sequence, are carried out (i) conversion of a precursor for the desired syn-2-(fur-2-yl)-2-methoxyiminoacetyl group into that said group, (ii) conversion of a $\Delta^2$ isomer into the desired $\Delta^3$ isomer, (iii) removal of any carboxyl blocking groups, and (iv) reduction of a compound in which B is $> S \rightarrow 0$ to form a B= >S compound; and (D) recovering the desired compound, after separation of syn and anti isomers if necessary, and if desired after conversion of the compound to a non-toxic derivative thereof.

Where $R^1$ is a carboxyl blocking group it may be the residue of an ester-forming alcohol (aliphatic or araliphatic), phenol, silanol or stannanol or a symmetrical or mixed anhydride group derived from an appropriate acid.

Non-toxic derivatives of the compounds of formula I may be formed in any convenient way. For example base salts may be formed by reaction of the cephalosporin acid with sodium or potassium 2-ethylhexanoate. Biologically acceptable ester derivatives may be formed using conventional esterifying agents. 1-Oxides may be formed by treatment of the corresponding cephalosporin sulphide with an appropriate oxidising agent, for example with a peracid such as metaperiodic, peracetic, monoperphthalic or m-chlorperbenzoic acid, or with t-butyl hypochlorite, conveniently in the presence of a weak base such as pyridine.

One may condense an acylating agent corresponding to the acid of formula (III) with an amino compound of formula (II) where B and the dotted line have the above defined meanings and $R^1$ is hydrogen or a carboxyl blocking group or a derivative thereof, e.g. a salt such as a tosylate or an N-silyl derivative, the condensation optionally being effected in the presence of a condensation agent, and being followed, if necessary, by removal of a carboxyl blocking group $R^1$.

Compounds of formula I may thus be prepared by employing as the acylating agent an acid halide, particularly an acid chloride or bromide, corresponding to the acid (III). Such acylations may be effected at temperatures of from −50° to +50° C, preferably −20° to +30° C. The acylation may be effected in aqueous or nonaqueous media.

Acylation with an acid halide may be effected in the presence of an acid binding agent, e.g. a tertiary amine such as triethylamine or dimethylaniline, an inorganic base such as calcium carbonate or sodium bicarbonate, or an oxirane, which serves to bind hydrogen halide liberated in the acylation reaction. Where an oxirane is employed for this purpose this is preferably a lower-1,2-alkylene oxide such as ethylene oxide or propylene oxide.

The free acid form of a compound of formula (III) may itself be used as the acylating agent. Such acylations are desirably conducted in the presence of, for example, a carbodiimide such as N,N'-diethyl-, dipropyl- or diisopropylcarbodiimide, N,N'-dicyclohexylcarbodiimide, or N-ethyl-N'-γ-dimethylaminopropylcarbodiimide, a carbonyl compound such as carbonyldiimidazole; or an isoxazolinium salt such as N-ethyl-5-phenylisoxazolinium-3'-sulphonate or N-t-butyl-5-methylisoxazolinium perchlorate. The condesation reaction is desirably effected in an anhydrous reaction medium, e.g. methylene chloride, dimethylformamide or acetonitrile.

Acylation may also be effected with other amide-forming derivatives of the free acid (III) such as, for example, a symmetrical anhydride or mixed anhydride, e.g. with pivalic acid or formed with a haloformate such as a lower alkylhaloformate. The mixed or symmetrical anhydrides may be generated in situ. For example, a mixed anhydride may be generated using N-ethoxycarbonyl-2-ethoxy-1,2-dihydroquinoline. Mixed anhydrides may also be formed with phosphorus acids (for example phosphoric or phosphorous acids), sulphuric acid or aliphatic or aromatic sulphonic acids (for example p-toluenesulphonic acid).

If desired, one can first prepare a compound of formula

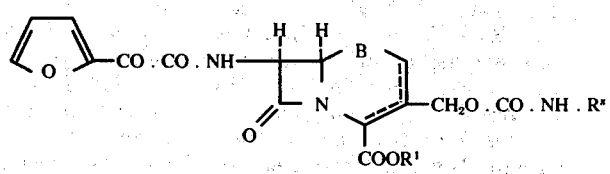

(where B, $R^1$, $R^s$ and the dotted line have the above defined meanings) and then effect reaction of the compound of formula (V) with methoxylamine followed if necessary by removal of the group $R^1$. The reaction product may be separated to give the required syn isomer before or after removal of $R^1$.

The reaction of the 3-hydroxymethyl cephalosporin (IV) with an isocyanate of formula $R^s$.NCO (wherein $R^s$ has the above defined meaning), may be in the presence of a lower ($C_1$–$C_4$) trialkylamine. The reaction may be effected at a temperature in the range −50° to +105° C, conveniently from 0° to +25° C.

The reaction may be effected in a substantially inert organic solvent e.g. an N,N-substituted amide, a halogen hydrocarbon or an ether. Reactions of this type are described for example in U.S. Pat. No. 3,355,452.

3-HYdroxymethyl starting materials for use in the process of this embodiment of the invention may be prepared by, for example, the methods described in British Pat. No. 1,121,308, and Belgian Pat. No. 783,449.

As indicated above, starting materials of formula II may if desired be employed in the form of acid addition salts, e.g. with hydrochloric, hydrobromic, sulphuric, nitric, phosphoric, toluene-p-sulphonic or methane sulphonic acids.

Any blocking group substituting the 4-carboxy group of compounds of formula II, IV and V is desirably a group which may readily be split off at a later stage of a reaction sequence and advantageously is a group containing 1–20 carbon atoms. Suitable blocked carboxyl groups are well known in the art, a list of representative groups being included in our aforementioned Belgian Pat. No. 783,449. Preferred blocked carboxyl include aryl lower alkoxycarbonyl groups such as p-methoxybenzyloxycarbonyl, p-nitrobenzyloxycarbonyl and diphenylmethoxycarbonyl; lower alkoxycarbonyl groups such as t-butoxycarbonyl; and lower haloalkoxycarbonyl groups such as 2,2,2-trichloroethoxycarbonyl. The carboxyl blocking group may subsequently be removed by any of the appropriate methods disclosed in the literature; thus, for example, acid or base catalysed hydrolysis is applicable in many cases, as are enzymically catalysed hydrolyses.

Where at the end of a given preparative sequence compounds are obtained wherein B is > S → O and a compound is desired in which B is > S conversion to a sulphide may for example, be effected by reduction of the corresponding acyloxysulphonium or alkyloxysulphonium salt prepared in situ by reaction with e.g. acetyl chloride in the case of an acetoxysulphonium salt, reduction being effected by, for example, sodium dithionite or by iodide ion as in a solution of potassium iodide in a water miscible solvent e.g. acetic acid, tetrahydrofuran, dioxan, dimethylformamide or dimethylacetamide. The reaction may be effected at a temperature of −20° to +50° C.

Where the resultant compound is a ceph-2-em-4-carboxylic ester the desired ceph-3-em compound may be (V)

obtained by treatment of the former with a base.

The antibiotic compounds according to the invention may be formulated for administration in any convenient way, by analogy with other antibiotics and the invention therefore includes within its scope a pharmaceutical composition comprising an antibacterial compound of formula I or a non-toxic derivative e.g. salt or biologically acceptable ester thereof adapted for use in human or veterinary medicine. Such compositions may be presented for use in conventional manner with the aid of any necessary pharmaceutical carriers or excipients.

The antibiotic compounds according to the invention may be formulated for injection and may be presented in unit dose form in ampoules, or in multi-dose containers with an added preservative. The compositions may take such forms as suspensions, solutions, emulsions in oily or aqueous vehicles, and may contain formulatory agents such as suspending, stabilising and/or dispersing agents. Alternatively the active ingredient may be in powder form for reconstitution with a suitable vehicle, e.g. sterile, pyrogen-free water, before use.

For veterinary medicine the compositions may, for example, be formulated as intramammary preparations in either long acting or quick-release bases.

In general the compositions may contain from 0.1% upwards, preferably from 10–60% of the active material, depending on the method of administration. Where the compositions comprise dosage units, each unit will preferably contain 50–1500mg. of the active ingredient. The dosage as employed for adult human treatment will preferably range from 500–4000 mg. per day, depending on the route and frequency of administration.

The compounds according to the invention may be administered in combination with other compatible therapeutic agents such as antibiotics, for example penicillins, other cephalosporins or tetracyclines.

The following examples illustrate the invention. All temperatures are in ° C, and melting points were determined on a Kofler block. Structures were also confirmed by infrared and proton magnetic resonance spectroscopy. Ultraviolet spectra were measured in pH6 phosphate buffer.

EXAMPLE 1

(6R,7R)-3-(2-chloroethylcarbamoyloxymethyl)7-[2-(fur-2-yl)-2-methoxyiminoacetamido]ceph-3-em-4-carboxylic Acid (syn isomer)

A solution of (6R,7R)-7-[2-(fur-2-yl)-2-methoxyiminoacetamido]-3-hydroxymethylceph-3-em-4-carboxylic acid (syn isomer) (1.50 g) in N,N-dimethylformamide (30 ml, purified by filtration through basic alumina) was cooled to 5° and was treated with triethylamine (1.1 ml) and 2-chloroethyl isocyanate (1.66 g). The reaction was stirred for 1 hour at 5° when the icebath was removed and stirring continued for 1.5 hours at ca. 20°. The solution was partitioned between aqueous sodium bicarbonate solution (3%, 100 ml) and ethyl acetate (100 ml). The layers were separated and the aqueous solution was washed with ethyl acetate (3 × 100 ml), then covered with ethyl acetate (100 ml) and acidified to pH 1.8 with concentrated hydrochloric acid. The layers were separated and the aqueous layer extracted with further ethyl acetate (4 × 100 ml). The combined organic extracts were washed with water (5 × 150 ml) and saturated sodium chloride solution (100 ml) and dried (MgSO$_4$), and the solvent was removed in vacuo to give a yellow froth which was triturated with ether (50 ml) to give the title compound as a yellow powder (0.59 g [$\alpha$]$_D$ + 40° (c 1, DMSO); $\lambda_{max}^{pH6}$ 275 nm ($\epsilon$ 17,400).

EXAMPLE 2

(6R,7R)-3-(3-Chloropropylcarbamoyloxymethyl)-7-[2-(fur-2-yl)-2-methoxyiminoacetamido]ceph-3-em-4-carboxylic Acid (syn isomer)

A stirred suspension of (6R,7R)-7-[2-(fur-2-yl-2-methoxyiminoacetamido]-3-hydroxymethylceph-3-em-4-carboxylic acid (syn isomer) (953 mg) in dry dichloromethane (50 ml) was treated with tri-n-butyl-tin oxide (743 mg, ca. 0.65 ml) and a yellow solution was obtained after 30 minutes. 3-Chloropropyl isocyanate (1.19 g) was added to the reaction mixture. After 2 hours a further portion of 3-chloropropyl isocyanate (595 mg) was added and further ca. 60 hours t.l.c. (chloroform:methanol:formic acid = 22:4:1) indicated that all starting material had been consumed. The reaction mixture was washed with 2N-hydrochloric acid (50 ml), water (25 ml) and extracted with aqueous sodium hydrogen carbonate solution (2 × 25 ml). The combined aqueous extracts were layered with ethyl acetate (50 ml) and acidified to pH 2 by addition of concentrated hydrochloric acid. The organic phase was separated and the aqueous phase re-extracted with ethyl acetate (50 ml). The combined organic extracts were washed with saturated brine (2 × 25 ml), dried (magnesium sulphae) and evaporated in vacuo to give a yellow foam (245 mg). T.l.c. indicated that hydrolysis of the tin ester was incomplete so the dichloromethane solution was stirred with 2N hydrochloric acid (50 ml) for 2 hours and worked up as before to give a further crop of yellow foam (188 mg). Combination of the foams and trituration with di-isopropyl ether afforded the title compound (334 mg) as a yellow solid m.p. 94° to 102°, [$\alpha$]$_D^{20}$ + 32.3° (c 0.5, DMSO), $\lambda_{max}$ 273 nm ($\epsilon$ 12,600) with an inflection at 281 nm ($\epsilon$ 12,170). A sample of the title compound (200 mg) was dissolved in propan-2-ol (2ml) and filtered to remove insoluble material. Addition of a solution of sodium-2-ethylhexanoate (67 mg) in propan-2-ol (1 ml) to the above solution off the cephalosporin caused the immediate crystallisation of a white solid. Crystallisation was completed by cooling the mixture to ca. 0° for 1 hour; the solid was filtered off, washed with propan-2-ol (3 ml) and dried to yield the sodium salt of the title compound (145 mg) [$\alpha$]$_D^{20.5}$ + 38.4° (c 0.51 in DMSO), $\lambda_{max}$ (pH 6 buffer) 273 nm ($\epsilon$ 16,420).

EXAMPLE 3

(6R,7R)-3-Chloromethylcarbamoyloxymethyl-7-[2-(fur-2-yl)-2-methoxyiminoacetamido]ceph-3-em-4-carboxylic Acid (syn isomer)

Triethylamine (505 mg, 0.69 ml) and chloromethyl isocyanate (2.73 g) were added to a solution of (6R,7R)-7-[2-(fur-2-yl)-2-methoxyimino acetamido]-3-hydroxymethylceph-3em-4-carboxylic acid (syn isomer) (1.906 g) in dry N,N dimethylformamide (25 ml). The reaction appeared complete (by t.l.c.) after ca. 5 minutes and was worked up after 30 minutes by pouring into 2N-hydrochloric acid (50 ml) and ethyl acetate (50 ml). The organic layer was retained and the aqueous layer re-extracted with ethyl acetate (25 ml). The organic layers were combined, washed with water (50 ml) and extracted with saturated aqueous sodium hydrogen carbonate solution (2 × 25 ml). The combined aqueous extracts were layered with ethyl acetate and acidified to pH 2 by addition of concentrated hydrochloric acid. The organic phase was separated and the aqueous phase re-extracted with ethyl acetate (25 ml). The combined organic extracts were washed with saturated brine (2 × 25 ml), dried (magnesium sulphate) and evapourated in vacuo to give a yellow gum (220 mg). Addition of di-isopropyl ether to a solution of the gum in ethyl acetate afforded the title compound, m.p. 169° to 176°, [$\alpha$]$_D^{20}$ + 38.9° (DMSO, c 0.49), $\lambda_{max}$ (pH 6 phosphate buffer) 277.5 nm ($\epsilon$ 16,550).

We claim:

1. A compound selected from the group consisting of a cephalosporin antibiotic of the formula

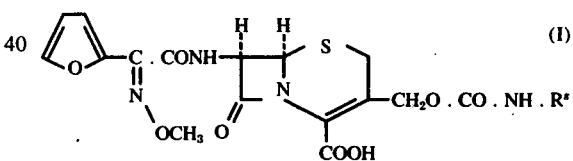

wherein R$^s$ represents a C$_1$-C$_4$ alkyl group substituted by chlorine, and a physiologically acceptable salt or oxide thereof.

2. The compound of claim 1 which is (6R,7R)-3-(2-chloroethylcarbamoyloxymethyl)-7-[2-(fur-2-yl)-2-methoxyiminoacetamido]ceph-3-em-4-carboxylic acid (syn isomer).

3. The compound of claim 1 which is sodium (6R,7R)-3-(2-chloroethylcarbamoyloxymethyl)-7-[2-(fur-2-yl)-2-methoxyiminoacetamido]3-em-4-carboxylate (syn isomer).

4. The compound of claim 1 which is (6R,7R)-3-chloromethylcarbamoyloxymethyl-7-[2-(fur-2-yl)-2-methoxyiminoacetamido]ceph-3-em-4-carboxylic acid (syn isomer).

5. The compoundof claim 1 which is (6R,7R)-3-(3-chloropropylcarbamoyloxymethyl)-7-[2-(fur-2-yl)-2-methoxyiminoacetamido]ceph-3-em-4-carboxylic acid (syn isomer).

6. The compound of claim 1 which is sodium (6R,7R)-3-(3-chloropropylcarbamoyloxymethyl)-7-[2-(fur-2-yl)-2-methoxyiminoacetamido]ceph-3-em-4-carboxylate (syn isomer).

* * * * *